United States Patent [19]

Ebata et al.

[11] Patent Number: 4,950,801
[45] Date of Patent: Aug. 21, 1990

[54] PROCESS FOR PRODUCING ALPHA-HYDROXYCARBOXYLIC ACID AMIDE

[75] Inventors: Shuji Ebata; Hiroyuki Hirayama; Hirofumi Higuchi; Toshio Kondo; Koichi Kida, all of Niigata, Japan

[73] Assignee: Mitsubishi Gas Chemical Company, Inc., Tokyo, Japan

[21] Appl. No.: 456,312

[22] Filed: Dec. 26, 1989

[30] Foreign Application Priority Data

Jan. 19, 1989 [JP] Japan .................................... 1-08714
Jan. 25, 1989 [JP] Japan .................................... 1-13897

[51] Int. Cl.$^5$ .......................................... C07C 102/08
[52] U.S. Cl. .................................................. 564/126
[58] Field of Search ........................................ 564/126

[56] References Cited

U.S. PATENT DOCUMENTS 2,415,645  2/1947  Lichtenwalter et al. ............ 564/126
3,794,682  2/1974  Barber ................................. 564/126

*Primary Examiner*—Glennon H. Hollrah
*Assistant Examiner*—Scott C. Rand
*Attorney, Agent, or Firm*—Frishauf, Holtz, Goodman & Woodward

[57] ABSTRACT

Disclosed is a process for producing α-hydroxy-carboxylic acid amide represented by the formula (I):

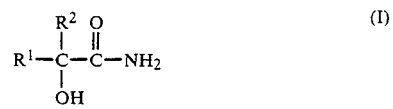

wherein $R^1$ and $R^2$ are as defined in the specification, by a catalytic hydration reaction of cyanohydrin represented by the formula (II):

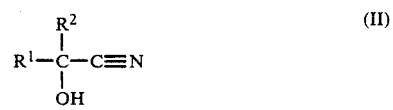

which comprises using a modified manganese dioxide containing one or more of an alkali metal element and an alkaline earth element in an amount of 0.05 to 0.5 based on the manganese element in terms of atomic ratio.

7 Claims, No Drawings

PROCESS FOR PRODUCING ALPHA-HYDROXYCARBOXYLIC ACID AMIDE

BACKGROUND OF THE INVENTION

1. Field of the Invention

The present invention relates to a process for producing an α-hydroxycarboxylic acid amide. More specifically, it relates to a process for producing an α-hydroxycarboxylic acid amide by a hydration reaction of cyanohydrin in liquid phase.

α-Hydroxycarboxylic acid amide becomes a starting material for the production of α, β-unsaturated carboxylate via α-hydroxycarboxylate. In particular, when α-hydroxysobutyramide is used as a starting material, methyl methacrylate can be obtained via methyl α-hydroxyisobutyrate which is finally converted into poly(methyl methacrylate), having an excellent resin characteristic and industrially great importance and uses.

2. Description of the Related Arts

As a catalyst for a hydration reaction of cyanohydrin to produce the corresponding α-hydroxycarboxylic acid amide, manganese dioxide is disclosed in West Germany Pat. No. 2,131,813. In addition, δ-type manganese dioxide used as a catalyst for a hydration reaction of acetone cyanohydrin is disclosed in U.S. Pat. No. 4,018,829.

Moreover, Japanese patent application Laid-Open Nos. 57534/1988 and 57535/1988 disclosed methods for preparing manganese dioxide catalysts in which zinc is incorporated into manganese dioxide or potassium permanganate is reduced with hydrochloric acid. However, when the manganese dioxide prepared by the above methods is used as a catalyst as it was in the reaction, there are problems in that catalytic activity is insufficient so a large amount of the catalyst is required to be used, the yield of the desired amide is low, and the catalytic activity is rapidly lowered in a relatively short period of time. Accordingly, the above manganese dioxide has not yet been used in practice.

The present inventors have found that an activity and a lifetime of a manganese dioxide catalyst are closely related to the amounts of an alkali metal element and/or an alkaline earth element caused to coexist in the catalyst when producing α-hydroxycarboxylic acid amide from cyanohydrin. In addition, present inventors have found that the lifetime of the catalyst can be improved by adjusting the hydrogen ion concentration (pH) of a starting material for the hydration reaction. The present invention can be accomplished based on the above findings.

SUMMARY OF THE INVENTION

An object of the present invention is to provide a process for efficiently producing α-hydroxycarboxylic acid amide from cyanohydrin.

An another object of the present invention is to provide a process for producing α-hydroxycarboxylic acid amide industrially using a catalyst having a high activity and a long life.

The present invention relates to: in a process for producing α-hydroxycarboxylic acid amide represented by the formula (I):

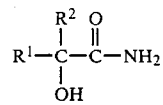

wherein $R^1$ represents a hydrogen or an aliphatic hydrocarbon group having 1 to 10 carbon atoms, and $R^2$ represents an aliphatic, alicyclic or aromatic hydrocarbon group having 1 to 10 carbon atoms, by a catalytic hydration reaction of cyanohydrin represented by the formula (II):

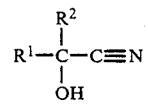

wherein $R^1$ and $R^2$ have the same meanings as defined above,
the improvement which comprises using, as a catalyst, a modified manganese dioxide containing at least one element selected from alkali metal elements and alkaline earth elements.

DESCRIPTION OF THE PREFERRED EMBODIMENTS

The process of the present invention is explained in more detail in the following.

The cyanohydrin represented by the formula (II) to be used in the present invention can be easily prepared by a reaction of an oxo compound represented by the formula (III):

wherein $R^1$ and $R^2$ have the same meanings as defined above, with hydrogen cyanide in the presence of a basic catalyst.

The modified manganese dioxide catalyst to be used in the present invention can be prepared as shown below.

It has already been described that manganese dioxide is used in the hydration reaction of cyanohydrin, and it is known that manganese dioxide is a manganese oxide existing between $MnO_{1.7}$ to $MnO_2$ and has crystal structures of α, β, δ, ε, etc. Furthermore, in the manganese dioxide, a transition between each phase or a change in crystallinity occurs so that its structure is very complicated and varied. Though manganese dioxide is present in nature, manganese dioxides prepared by oxidizing divalent manganese or by reducing VII valent manganese are suitable for a catalyst. Among them, manganese dioxide prepared by reducing VII valent manganese is preferred because homogeneous material can be obtained, and its crystal type, its specific surface area, and kinds and amounts of an alkali and alkaline earth elements to be incorporated can be easily controlled.

The manganese dioxide catalyst of the present invention is manganese dioxide containing an alkali metal element and/or an alkaline earth element preferably in an amount of 0.05 to 0.5 based on the manganese element in terms of atomic ratio, and having a large specific surface area, low crystallinity and an amorphous or a nearly amorphous state.

Manganese dioxide can be prepared under either acidic or alkaline conditions, but acidic conditions are preferred. When the manganese dioxide is prepared under alkaline conditions, it is desirable to wash the manganese dioxide with a diluted sulfuric acid etc. before using in the hydration reaction, in order to control the decomposition of cyanohydrin.

When the contents of an alkali metal element and/or an alkaline earth element in the prepared manganese dioxide are less than 0.05 in terms of atomic ratio mentioned above, the manganese dioxide is suspended in an aqueous solution of an alkali metal element and/or alkaline earth element and then heated. By such procedures, a part of the manganese dioxide is exchanged with an ion of an alkali metal element and/or an alkaline earth element to prepare a modified manganese dioxide containing the desired amounts of an alkali metal element and/or an alkaline earth element.

The metal salt of an alkali and/or alkaline earth metal to be added for preparation of the catalyst can be selected from water-soluble salts. Among them, a sulfate or a nitrate is particularly preferred.

The aqueous solution for the ion-exchange can be either acidic or alkaline. But when the ion-exchange is carried out under alkaline conditions, the modified manganese dioxide is preferably subjected to post-washing with a diluted sulfuric acid or a diluted nitric acid. In addition, the processing conditions of the ion-exchange are atmospheric pressure or under elevated pressure at a temperature of 30 to 250° C, preferably 50 to 200° C.

If the temperature is lower than the above range, the efficiency of ion-exchange is low. On the other hand, if the temperature is higher than the above range, the specific surface area of the manganese dioxide is undesirably reduced.

The above heat treatment is also effective for regenerating a manganese dioxide catalyst which has been deactivated by the hydration reaction of cyanohydrin.

In the present invention, the modified manganese dioxide prepared as mentioned above is used in the hydration reaction of cyanohydrin as a fixed-bed catalyst by tabletting or extrusion molding, or as a slurry catalyst in the form of a powder in a batch system or flow system.

The hydration reaction using the modified manganese dioxide catalyst of the present invention is usually carried out in the system with excess water.

That is, the amount of cyanohydrin in the starting mixture or solution for the hydration reaction is 10 to 60% by weight, preferably 20 to 50% by weight. In addition, when the oxo compound of the formula(III) which corresponds to the cyanohydrin of the formula(II) is present in an amount of 5 to 30% by weight in the starting solution, decomposition reaction of the cyanohydrin is inhibited whereby the yield of α-hydroxycarboxylic acid amide increases.

The starting solution to be used in the present invention can be prepared as shown below.

Cyanohydrin commercially available such as acetone cyanohydrin is added with a mineral acid such as a sulfuric acid or a phosphoric acid as a stabilizer, and when it is mixed with water or ketone such as acetone to prepare a starting solution, the pH of the starting solution becomes 1 to 3. In the process of the present invention, such a starting solution can be used without any treatment, but is preferably used after adjusting the pH to the range of 4 to 8.

In order to adjust the pH of the starting solution to 4 to 8, acidic substances contained in cyanohydrin should be removed. The following methods are performed to obtain a starting solution having the desired pH.

Method (1) : a method in which the starting solution is prepared by adding predetermined amounts of water and a ketone such as acetone to a cyanohydrin from which the mineral acid has been removed by distillation;

Method (2) : a method in which the starting solution is prepared by passing a crude starting solution comprising cyanohydrin with predetermined amounts of water and ketone such as acetone added thereto through a layer filled with a basic absorbent or an anion-exchange resin to remove the mineral acid; and Method (3) : a method in which the starting solution is prepared by adding an alkali such as sodium hydroxide or potassium hydroxide to a crude starting solution comprising cyanohydrin with predetermined amounts of water and ketone such as acetone to neutralize the mineral acid therein.

The starting solution obtained by the above methods has a pH in the range of 4 to 8 and the process of the present invention can be carried out effectively by using it.

In addition, in the above Methods (2) and (3), the starting solution can be prepared by previously removing the mineral acid only from cyanohydrin, and then adding predetermined amounts of water and ketone such as acetone thereto.

Furthermore, a method for preparing the starting solution by which the process of the present invention can be carried out suitably is shown below.

Method (4) : this is a method for adjusting the pH of the starting solution by circulating a part of the reaction product solution. This method utilizes the fact that an α-hydroxycarboxylic acid amide such as α-hydroxyisobutyramide as the reaction product is a weak alkaline. Therefore, the pH of the starting solution to be supplied to a catalytic layer can be raised by the method. As a result, the pH of the starting solution can be maintained in the range that the process of the present invention can proceed efficiently.

When the reaction is carried out by using the starting solution in which a part of the reaction product solution is circulated, the conversion of cyanohydrin is lowered slightly compared with using the other starting solution in the same reaction conditions so that the one pass yield of α-hydroxycarboxylic acid amide such as α-hydroxyisobutyramide is slightly lowered. However, the pH of the starting solution is automatically maintained in a suitable range so that a high selectivity to α-hydroxycarboxylic acid amide such as α-hydroxyisobutyramide can be maintained. In addition, there are advantages in that the reaction temperature can be controlled easily because of depressing temperature increase due to heat of hydration reaction. Therefore, Method (4) is remarkably advantageous in practical use.

The amount of the reaction product solution circulating in the method is 0.1 to 100 times, preferably 0.5 to 10 times based on an amount of starting solution consisting of cyanohydrin and predetermined amounts of water and ketone such as acetone.

The above four methods of adjusting the pH of the starting solution can be used singly or in a combination of two or more, and methods which can be used in the present invention are not limited thereto.

The process of the present invention is effectively carried out in a pH range of 4 to 8 for the starting solution. If the pH of the starting solution is less than 4, the lifetime of the catalyst may sometimes be shortened. On the other hand, in case that the pH exceeds 8, there may sometimes occur disadvantages in that the stability of cyanohydrin deteriorates and colorations or amounts of impurities such as by-products increase.

In the process of the present invention, the reaction temperature is not particularly limited, but should be in the range of 20 to 100° C, preferably 40 to 80° C. At a temperature lower than the above range, the reaction rate becomes slow, while at a temperature higher than the above, by-products caused by the decomposition of cyanohydrin undesirably increase in most cases.

In the reaction product solution obtained by the process of the present invention, in addition to the desired compound of α-hydroxycarboxylic acid amide, there are contained cyanohydrin such as unreacted acetone cyanohydrin, water, or acetone as a solvent, with a small amount of acetone and formamide as by-product. These by-products have lower boiling points than α-hydroxycarboxylic acid amide, so the desired compound of α-hydroxycarboxylic acid amide can easily be separated and recovered by a method in which all of the by-products are distilled out or a method in which after a part of the by-products is distilled out, crystallization is carried out.

According to the process of the present invention, a high activity and a long life for catalyst can be achieved in the preparation of α-hydroxycarboxylic acid amide from cyanohydrin. Therefore it has significance for industry. In addition, by adjusting the hydrogen ion concentration pH of the starting solution within the range of 4 to 8, a marked prolongation of the catalyst life and further improvement of reaction efficiency can be realized.

In the following, the process of the present invention is described in more detail by referring to Examples and Comparative examples. The reagents used are all of a special grade unless otherwise specifically mentioned. In addition, a deionized water having a specific resistance of 18 MΩ.cm is used as water.

COMPARATIVE EXAMPLE 1

(1) Preparation of a catalyst: In 700 g of water was dissolved 55.3 g of potassium permanganate, and then 42.9 g of conc. sulfuric acid was added little by little. Next, 16.8 g of methanol was gradually added at 20 to 25° C. and the mixture was stirred at room temperature for 3 hours. The resulting slurry was subjected to suction filtration, and the resulting cake was washed with 700 g of water three times and then dried at 110° C. overnight to give 23.8 g of black-brown bulk manganese dioxide. A part thereof is taken out, dissolved in conc. hydrochloric acid and its potassium ion and manganese ion contents were measured by an atomic absorption analyzer to give the results of potassium/manganese =0.018 (atomic ratio).

(2) Reaction : The manganese dioxide obtained by the above procedure was crushed and regulated in a range of 10 to 20 meshes. Three point five grams of this material was packed into a glass tube having an inner diameter of 10 mm to which a jacket is attached. Hot water (60° C) was passed into this jacket.

A starting material acetone cyanohydrin, having a purity of 99.5% (containing 500 ppm of sulfuric acid) for industrial use was employed after distillation under a reduced pressure of 5.5 mmHg at a temperature of 70 to 76° C.

A starting solution obtained by mixing 20 g of the above acetone cyanohydrin, 60 g of water and 20 g of acetone and having a pH of 4.8 was passed through a tubular reactor at a flow rate of 5 g/hr. When a composition of the reaction solution after 5 hours was analyzed using high-performance liquid chromatography, the results were 22.0% by weight of α-hydroxyisobutyramide, 0.4% by weight of acetone cyanohydrin, 21.0% by weight of acetone and 0.7% by weight of formamide. This corresponds to an α-hydroxyisobutyramide yield of 91% (based on the starting acetone cyanohydrin).

When the reaction was further continued, and the composition of the reaction solution was analyzed again after one week, the yield of α-hydroxyisobutyramide had decreased to 0.3%.

EXAMPLE 1

(1) Preparation of a catalyst: Dissolved in 70 g of water was 3.11 g of potassium sulfate, and then 2.61 g of conc. sulfuric acid was added. To the resulting solution was suspended the 15.9 g of powdery manganese dioxide prepared in Comparative example 1 and the resulting suspension was stirred at 80° C. for 3 hours while heating. Suction filtration was carried out after cooling to room temperature, and the resulting cake was washed three times with 100 g of water and then dried at 110° C. overnight to give 13.4 g of black-colored bulk manganese dioxide. When its potassium content and manganese content were measured, the result was potassium/manganese =0.21 (atomic ratio).

(2) Reaction: The reaction was carried out in the same manner as in Comparative example 1 except that 3.5 g of the manganese dioxide obtained by (1) above was used. The results showed that the yields of α-hydroxyisobutyramide after 5 hours and one week were both 95%.

EXAMPLES 2 to 6

In the same manner as in Example 1 except that potassium sulfate in Example 1 was replaced with another alkali metal sulfate or alkaline earth nitrate, the catalysts were prepared and hydration reaction of acetone cyanohydrin were carried out. The results are shown in Table 1.

TABLE 1

| No. | Alkali or alkaline earth metal salt | M/Mn* (Atomic ratio) | Yield of α-hydroxy-isobutyramide After 5 hours | After one week |
| --- | --- | --- | --- | --- |
| Example 2 | $Rb_2SO_4$ | 0.09 | 93% | 91% |
| Example 3 | $Na_2SO_4$ | 0.12 | 95% | 95% |
| Example 4 | $Li_2SO_4$ | 0.15 | 96% | 95% |
| Example 5 | $Ca(NO_3)_2$ | 0.08 | 92% | 87% |
| Example 6 | $Mg(NO_3)_2$ | 0.08 | 92% | 83% |

*M represents metal in alkali or alkaline earth metal salt used.

COMPARATIVE EXAMPLE 2

(1) Preparation of a catalyst: Dissolved in 250g of water was 5.0g of potassium permanganate, and then 10g of 12 N hydrochloric acid was added at 55° C. little by little. The resulting precipitates were aged at 60° C. for 3 hours, and then filtered, washed with 200g of water three times and dried at 110° C. overnight to give 7.6g of black brown bulk manganese dioxide. This material had a potassium/manganese ratio (atomic ration) of 0.04.

(2) Reaction: The hydration reaction was carried out using 3.6g of the catalyst prepared as described above in the same manner as in Comparative example 1. The results showed that yields of α-hydroxyisobutyramide after 5 hours and one week were 88% and 57%, respectively.

COMPARATIVE EXAMPLE 3

(1) Preparation of catalyst: Dissolved in 120g of water was 19.2g of potassium permanganate to prepare solution A, and then solution B prepared by dissolving 22.2g of manganese sulfate tetra- to hexahydrate and 6.7g of potassium hydroxide in 30g of water was poured into above solution A at 70° C. as soon as possible. The resulting precipitates were filtered after stirring at 70° C. for 3 hours, and after washing three times with 200g of water, and then dried at 110° C. overnight to give 23.8 g of brown bulk manganese dioxide.

(2) Reaction: The hydration reaction was carried out using 3.5g of the catalyst prepared as (1) above in the same manner as in Comparative example 1.

The results showed that yields of α-hydroxyisobutyramide after 5 hours and one week were 74% and 41%, respectively.

EXAMPLE 7

(1) Preparation of a catalyst: Mixed in 100g of 1 M sulfuric acid was 10g of manganese dioxide obtained in Comparative example 3, and the mixture was stirred at room temperature for 2 days. The resulting precipitates were filtered and then washed and dried in the same manner as described for Comparative example 3 to give 9.6g of black-colored bulk manganese dioxide. This material had a potassium/manganese ratio (atomic ratio) of 0.12.

(2) Reaction: The hydration reaction was carried out in the same manner as described in Comparative example 3 except that 3.5g of the catalyst obtained by (1) above was used. The results showed that yields of α-hydroxyisobutyramide after 5 hours and one week were 91% and 89%, respectively.

EXAMPLE 8

(1) Preparation of a catalyst: To a solution obtained by dissolving 73.8g of potassium permanganate in 200 ml of a water was rapidly poured a mixture of 184g of 20% by weight manganese sulfate aqueous solution and 33g of conc. sulfuric acid at 70° C. The resulting precipitates were filtered after stirring at 90° C. for 3 hours, and then washed three times with 200 ml of water and dried at 110° C. overnight to give 21.5g of black-colored bulk manganese dioxide. This material had a potassium/manganese ratio (atomic ratio) of 0.13.

(2) Reaction: The hydration reaction was carried out in the same manner as in Comparative example 1 except that 3.3g of the catalyst obtained by (1) above was used.

The result showed that yields of α-hydroxyisobutyramide after 5 hours and one week were 94% and 93%, respectively.

EXAMPLE 9

(1) Preparation of a catalyst: Dissolved in 140g of water was 12.8g of sodium permanganate, and then 2.5g of conc. sulfuric acid was added thereto to prepare solution A. Then, solution B obtained by dissolving 22.2g of manganese sulfate tetra-to hexahydrate in 30 ml of water was poured into the above solution A at 70° C. and the resulting mixture was stirred at 80° C. for 3 hours. After cooling to room temperature and filtering, the resulting precipitates were washed three times with 200 ml of water and dried at 110° C. overnight to give 22.5g of black-colored bulk manganese dioxide. This material had a sodium/manganese ratio(atomic ratio) of 0.10.

(2) Reaction: The hydration reaction was carried out in the same manner as described in Comparative example 1 except that 3.5g of the catalyst obtained by (1) above was used, replacing acetone cyanohydrin with methyl ethyl ketone cyanohydrin, and replacing acetone with methyl ethyl ketone. The results showed that yields of 2-hydroxy-2-methylbutyramide after 5 hours and one week were 85% and 88%, respectively.

COMPARATIVE EXAMPLE 4

In the same manner as in Example 1 except that acetone cyanohydrin for industrial use was used without distillation, the catalyst was prepared and the hydration reaction of acetone cyanohydrin was carried out. The pH of the starting solution was 2.5.

The results showed that yields of α-hydroxyisobutyramide after 5 hours and one week were 91% and 22%, respectively.

EXAMPLE 10

In the same manner as in Example 1 except that undistilled acetone cyanohydrin was used as described in Comparative example 4 and a part of the reaction product solution was circulated into the starting solution to effect the reaction, the catalyst was prepared and the hydration reaction of acetone cyanohydrin was carried out. The pH of the solution supplied to the reactor was 4.5.

The results showed that yields of α-hydroxyisobutyramide after 5 hours and one week were 81% and 78%, respectively.

What is claimed is:

1. In a process for producing α-hydroxycarboxylic acid amide represented by the formula (I):

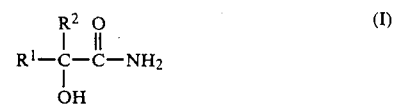

(I)

wherein $R^1$ represents a hydrogen or an aliphatic hydrocarbon group having 1 to 10 carbon atoms and $R^2$ represents an aliphatic, alicyclic or aromatic hydrocarbon group having 1 to 10 carbon atoms, by a catalytic hydration reaction of cyanohydrin represented by the formula (II):

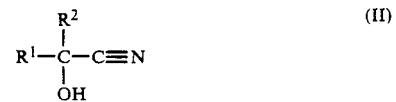

(II)

wherein $R^1$ and $R^2$ have the same meanings as defined above, the improvement which comprises using, as a catalyst, a modified manganese dioxide containing at least one element selected from alkali metal elements and an alkaline earth elements.

2. A process according to claim 1, wherein the cyanohydrin is acetone cyanohydrin.

3. A process according to claim 1, wherein the alkali metal element is at least one element selected from sodium and potassium.

4. A process according to claim 1, wherein the alkaline earth metal element is at least one element selected from magnesium and calcium.

5. A process according to claim 1, wherein the atomic ratio of the alkali metal element and alkaline earth element contained in the modified manganese dioxide to a manganese element is 0.05 to 0.5.

6. A process according to claim 1, wherein the hydrogen ion concentration pH of a cyanohydrin starting solution for hydration reaction is within the range of 4 to 8.

7. A process according to claim 1, wherein a part of a reaction product solution is circulated in a cyanohydrin starting solution for a hydration reaction.

* * * * *